US006355860B1

(12) United States Patent
Borysyuk et al.

(10) Patent No.: US 6,355,860 B1
(45) Date of Patent: *Mar. 12, 2002

(54) MATERIALS AND METHODS FOR AMPLIFYING AND ENHANCED TRANSCRIBING OF POLYNUCLEOTIDES IN PLANTS AND PORTIONS THEREOF

(75) Inventors: Mykola Borysyuk; Lyudmyla Borysyuk, both of East Brunswick; Ilya Raskin, Manalapan, all of NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/333,214

(22) Filed: Jun. 15, 1999

Related U.S. Application Data

(63) Continuation-in-part of application No. 09/097,541, filed on Jun. 15, 1998, now Pat. No. 6,100,092.

(51) Int. Cl.[7] .......................... C12N 5/04; C12N 15/82; C12N 15/90; C12N 15/69; A01H 5/00
(52) U.S. Cl. ................... 800/278; 435/69.1; 435/320.1; 435/419; 435/468; 536/24.1; 800/298
(58) Field of Search ............................... 435/69.1, 410, 435/419, 468, 320.1; 536/23.6, 23.1, 24.1; 800/278, 295, 298

(56) References Cited

U.S. PATENT DOCUMENTS 6,100,092 A * 8/2000 Borysyuk et al. ............ 435/468

FOREIGN PATENT DOCUMENTS

| AT | A 1695/96 | 9/1996 | ........... C12N/15/82 |
|---|---|---|---|
| EP | 0 243 553 | 11/1987 | ........... C12N/15/00 |
| WO | WO 84/02920 | 8/1984 | ........... C12N/15/00 |
| WO | WO 96/04392 | 2/1996 | ........... C12N/15/82 |
| WO | WO 98/13505 | 8/1996 | ........... C12N/15/82 |

OTHER PUBLICATIONS

Volkov, R.A., Genbank Accession No. Y08427, 1996.*

Borisjuk, N.V. et al., "Novel class of rDNA repeat units in somatic hybrids between Nicotiana and Atropa," Theor. Appl. Genet., 76:108–112 (1988).

Borisjuk, N.V. et al., "Nucleotide sequence of the potato rDNA intergenic spacer," Plant Mol. Biol. 21:381–384 (1993).

Borisjuk, N.V. et al., "Structural analysis of rDNA in the genus Nicotiana," Plant Molecular Biology, 35:655–660 (1997).

Borisjuk, N.V. et al., "Calreticulin expression in plant cells: developmental regulation, tissue specificity and intracellular distribution," Planta 206:504–514 (1998).

Christou, P., "Strategies for variety–independent genetic transformation of important cereals, legumes and woody species utilizing particle bombardment," Euphytica, 85:13–27 (1995).

Doelling, J.H. et al., "Functional analysis of *Arabidopsis thaliana* rRNA gene and spacer promoters in vivo and by transient expression," Proc. Natl. Acad. Sci. (USA), 90:7528–7532 (Aug. 1993).

Doelling, J.H. et al. "The minimal ribosomal RNA gene promoter of *Arabidopsis thaliana* includes a critical element at the transcription initiation site," The Plant Journal, 8(5):683–692 (1995).

Fan, H. et al., "In vitro transcription of plant RNA polymerase I–dependent rRNA genes is species–specific," The Plant Journal, 8(2):295–298 (1995).

Gruendler, P. et al., "rDNA Intergenic Region from *Arabidopsis thaliana*: Structural Analysis, Intraspecific Variation and Functional Implications," J. Mol. Biol., 221:1209–1222 (1991).

Haughn, G.W. et al., "Transformation with a mutant Arabidopsis acetolactate synthase gene renders tobacco resistant to sulfonylurea herbicides," Mol. Gen. Genet. 211:266–271 (1988).

Hemann, C. et al., "High–Copy Expression Vector Based on Amplification–Promoting Sequences," DNA and Cell Biology, 13(4):437–445 (1994).

Holst, A. et al., "Murine Genomic DNA Sequences Replicating Autonomously in Mouse L Cells," Cell, 52:355–365 (1988).

Hood, E.E. et al., "The Hypervirulence of *Agrobacterium tumefaciens* A281 Is Encoded in a Region of pTiBo542 Outside of T–DNA," J. Bacteriol., 168(3): 1291–1301 (1986).

(List continued on next page.)

*Primary Examiner*—Amy J. Nelson
*Assistant Examiner*—Ashwin Mehta
(74) *Attorney, Agent, or Firm*—Marshall, Gerstein & Borun

(57) ABSTRACT

Products and methods for amplifying target nucleic acids using cells derived from plants are disclosed. Also disclosed are methods for improving transcription of target nucleic acids beyond expectations based solely on target copy number, and the recovery of such expression products. The products include nucleic acids containing a plant-active Amplification Promoting Sequence (APS) and the methods exploit these products in amplifying target nucleic acids. The methods of the invention minimize operator intervention and exploit solar energy and the minimal nutrient needs of photoautotrophic organisms to provide inexpensive and indefinitely sustainable methods for producing a variety of amplified target nucleic acids and encoded products such as polypeptides.

17 Claims, 6 Drawing Sheets

OTHER PUBLICATIONS

Jackson, S.D. et al., "Protein–binding to reiterated motifs within the wheat rRNA gene promoter and upstream repeats," Plant Molecular Biology, 20:911–919 (1992).

Jähne, A. et al., "Genetic engineering of cereal crop plants: a review," Euphytica, 85:35–44 (1995).

Kellems, R.E., "Gene Amplification Strategies for Protein Production in Mammalian Cells," Methods in Molecular Genetics, 5:143–155 (1994).

Kneidl, C., et al., "An intrinsically bent region upstream of the transcription start site of the rRNA genes of *Arabidopsis thaliana* interacts with an HMG–related protein," Plant Mol. Biol. 27:705–713 (1995).

Lopes, T.S. et al., "High–copy–number integration into the ribosomal DNA of *Saccharomyces cerevisiae*: a new vector for high–level expression," Gene, 79:199–206 (1989).

Marilley, M. et al., "Common DNA structural features exhibited by eukaryotic ribosomal gene promoters," Nucl. Acids. Res., 24(12):2204–2211 (1996).

Meyer, J. et al., "Inhibition of HIV–1 replication by a high–copy–number vector expressing antisense RNA for reverse transcriptase," Gene, 129:263–268 (1993).

Perry, K.L. et al., "Transcription of tomato ribosomal DNA and the organization of the intergenic spacer," Mol. Gen. Genet. 221:102–112 (1990).

Reichel, C. et al., "Enhanced green fluorescence by the expression of an *Aequorea victoria* green fluorescent protein mutant in mono– and dicotyledonous plant cells," Proc. Natl. Acad. Sci.(USA), 93:5888–5893 (1996).

Sambrook et al., §§9.47–9.51 in Molecular Cloning: A Laboratory Manual, (Cold Spring Harbor Laboratory Press, Cold Spring Harbor, New York 1989).

Santangelo, G.M., et al., "Properties of Promoters Cloned Randomly from the *Saccharomyces cerevisiae* Genome", Mol. Cell. Biol. 8(10):4217–4224 (1988).

Sathasivan, K. et al., "Nucleotide sequence of a mutant acetolactate synthase gene from an imidazolinone–resistant *Arabidopsis thaliana* var. Columbia," Nucl. Acids Res. 18:2188 (1990).

Suzuki, A. et al., "Structural and Functional Characterization of the Intergenic Spacer Region of the rDNA in *Daucus carota*," Plant Cell Physiol. 37(2):233–238 (1996).

Vain, P. et al., "Foreign Gene Delivery Into Monocotyledonous Species," Biotechnology Advances, 13(4): 653–671 (1995).

Wanzenbock, E–M. et al., "Ribosomal transcription units integrated via T–DNA transformation associate with nucleolus and do not require upstream repeat sequences for activity in *Arabidopsis thaliana*," Plant J. 11(5):1007–1016 (1997).

Wegner, M. et al., "Cis–acting sequences from mouse rDNA promote plasmid DNA amplification and persistence in mouse cells: implication of HMG–I in their function," Nucl. Acids. Res., 17(23):9909–9932 (1989).

Zastrow, G. et al., "Distinct mouse DNA sequences enable establishment and persistence of plasmid DNA polymers in mouse cells," Nucl. Acids Res., 17(5):1867–1879 (1989).

* cited by examiner

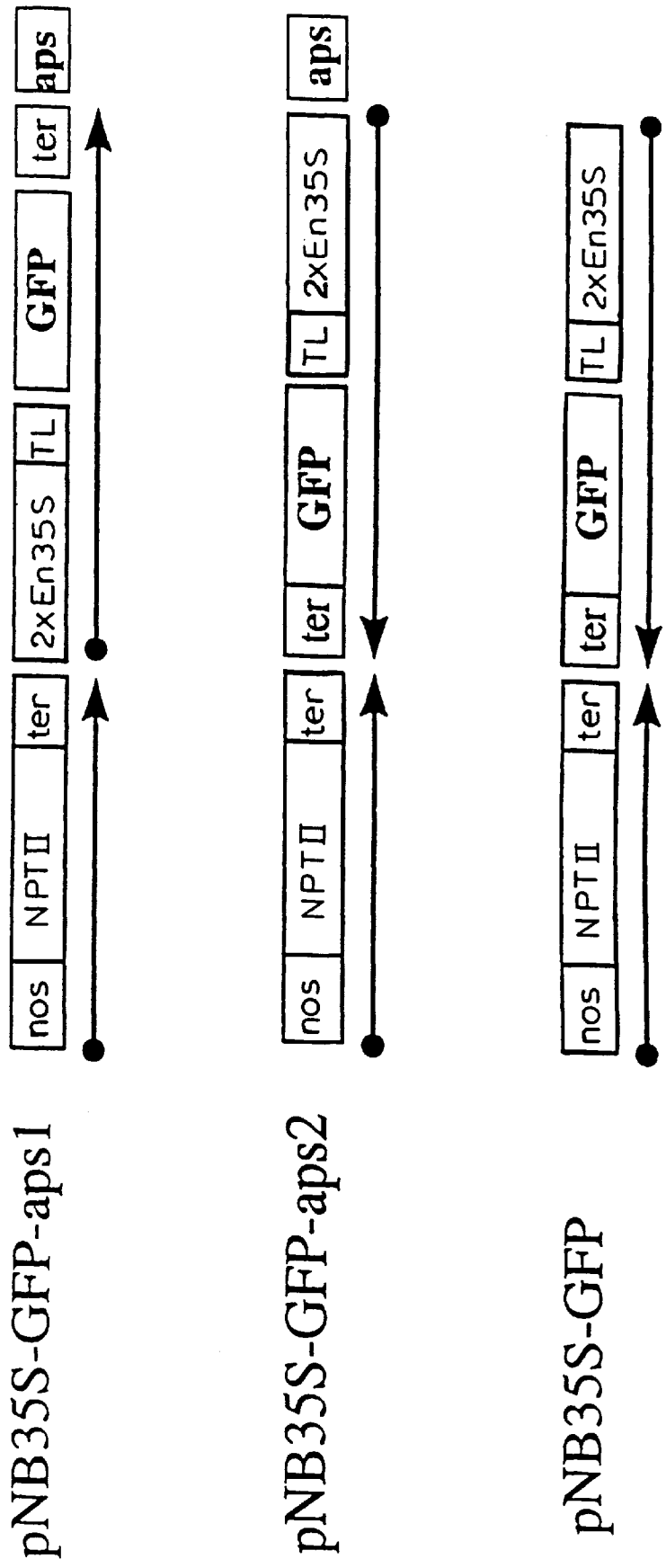

| Herbicide concentration | pNB-ALS aps | pNB-ALS | Wild type |
|---|---|---|---|
| 0 uM | 40 | 38 | 12 |
| 1 uM | 40 (100%) | 38 (100%) | 0 (0%) |
| 5 uM | 25 (63%) | 5 (13%) | 0 (0%) |
| 10 uM | 17 (42%) | 2 (5%) | 0 (0%) |
| 15 uM | 7 (22%) | 0 (0%) | 0 (0%) |
| 20 uM | 5 (12%) | 0 (0%) | 0 (0%) |

FIG. 6

MATERIALS AND METHODS FOR AMPLIFYING AND ENHANCED TRANSCRIBING OF POLYNUCLEOTIDES IN PLANTS AND PORTIONS THEREOF This application is a continuation-in-part of U.S. patent application Ser. No. 09/097,541 now U.S. Pat. No. 6,100,092, filed June 15, 1998.

FIELD OF THE INVENTION

The present invention relates to products and processes for amplification of nucleic acids and for expression of nucleic acids in plants.

BACKGROUND

Biomolecules such as complex proteins and nucleic acids have shown their value as products in such diverse fields as medical diagnostics/therapeutics and agriculture. Given the potential value of the products, it is not surprising that the efficient large-scale production of these biomolecules remains an active area of inquiry in biotechnology. Existing methods vary in their capacities to produce a desired biomolecule and these methods vary in terms of the costs required to achieve those levels of production. Production methods exhibiting lowered per unit production costs would provide improved approaches to the generation of biomolecules.

One strategy for improving biomolecule production is directed to maximizing the yield of the desired biomolecule. One type of approach to maximizing yield has focused on minimizing the loss of biomolecules in the production process. Recovery of active biomolecules such as polypeptides is frequently lowered due to chemical events (e.g., oxidation) and biochemical events (e.g., nuclease- or protease-mediated degradation). Thus, some production methods address these losses by adding, e.g., an anti-oxidant (β-mercaptoethanol or dithiothreitol) or an inhibitor of either nucleases (e.g., vanadium complexes) or proteases (e.g., phenylmethylsulfonylfluoride). Alternative approaches modify the expressed biomolecule to confer increased stability (e.g., alkylation). However, all of these interventions are costly.

Other strategies to lower unit costs have concentrated on improving the gross yield of a desired biomolecule. Towards that end, refinements to production methods have been developed that increase the raw production of, e.g., a polypeptide by improving the genetic expression of the desired product. For example, a variety of recombinant techniques have been used to operatively link a coding region for a desired polypeptide to a strong (i.e., active) expression control signal such as a promoter An alternative approach exploits the copy number effect by amplifying copies of a coding region to provide more "substrate" for expression. For example, Schimke et al., J. Biol. Chem. 263:5989–5992 (1988), disclosed a technique that involved a recombinant construct that linked the Dihydrofolate Reductase (DHFR) gene to a coding region of interest. Because DHFR quantity is positively correlated to resistance to the anti-cancer drug methotrexate, challenging cells containing the construct with methotrexate selected for cells that had amplified the construct, thereby producing more DHFR and more of the desired expression product.

Another strategy for amplification has been the development of transformation systems that result in multiple copies of an introduced DNA sequence integrating into a host genome. The ribosomal DNA (i.e., rDNA) locus is an attractive target for integration since it provides a promisingly high number of target sites for integration, extending upwards from approximately 100 copies in eukaryotes. Lopes et al., Gene 79:199–206 (1989). Some multiple copy transformation systems targeting rDNA have been established using unicellular eukaryotes (Tondravi et al., Proc. Natl. Acad. Sci. (USA) 83:4369–4373 (1986); Lopes et al., (1989); Tsuge et al., Gene 90:207–214 (1990)) and cultured mouse fibroblasts (Hemann et al., DNA and Cell Biol. 13:437–445 (1994), incorporated herein by reference. Plasmid vectors containing sequences homologous to an rDNA region dramatically increased the transformation efficiency of the yeast *S. cerevisiae* and the phytopathogenic fungus *Alternaria altenata*. Yeast cells transformed with an rDNA-based expression vector containing the homologous gene for pliosphoglycerate Vase (PGK) and a heterologous gene for thaumatin were shown to carry 100–200 copies of the introduced sequences per cell. Lopes et al., (1989). Under optimized conditions, the level of PGK in transformed cells was about 50% of total soluble protein. The yield of thaumatin in transformants exceeded by a factor of 100 the level of thaumatin observed in transformants carrying only a single thaumatin gene.

Hemann et al., (1994) extended this approach by developing a high-copy expression system for mouse L fibroblasts, thereby overcoming a variety of biochemical deficiencies in enzyme-deficient cell lines. The system relied on the inclusion of an amplification promoting sequence (muNTS1), derived from the nontranscribed spacer region of murine rDNA, in the transformation vector. Wegner et al., Nucl. Acids Res. 17:9909–9932 (1989), incorporated herein by reference. The muNTS1 was originally isolated from mouse rDNA by screening with a vector containing a truncated promoter driving the expression of a thyymidine lanase gene. The high copy number amplification was achieved by the 370-bp amplification promoting element (muNTS1). Holst et al., Cell 52:355–365 (1988). Under these conditions, muNTS1 promoted amplification of the integrated vector. Copy number determination showed that muNTS1 mediated a 40- to 800-fold amplification of the vector DNA in transfected L cells. Wegner et al. (1989). The high copy number resulted in increased expression levels of the reporter gene. Further, muNTS1 was reported to promote vector amplification without selective pressure for amplification. Meyer et al., Gene 129:261–268 (1993).

These approaches to biomolecule production have been implemented using host cells of fungal or animal origin. Frequently, a commercially desirable biomolecule is a eukaryotic (e.g., human) polypeptide requiring post-translational modifications such as glycosylation, phosphorylation, etc., that a yeast host cell cannot provide. The vast majority of the unmodified analogs of these desirable polypeptides lack activity and are of little commercial value. In contrast, animal cells are eukaryotic cells typically capable of properly modifying an expressed polypeptide such as a human polypeptide. Animal cells are heterotrophic cells, however, requiring the costly inputs of energy and nutrients. Additionally, animal cell and tissue cultures require the costly maintenance of sterile conditions to prevent destructive contamination. With respect to transgenic animals, sterile conditions may not need to be maintained but, in addition to ethical concerns, the use of transgenic animals as polypeptide factories requires the costly raising of the animals and the costly isolation of the desired biomolecule.

Therefore, a need continues to exist in the art for biomolecule production methods that optimize the yield of a biomolecule, preferably in active form.

SUMMARY OF THE INVENTION

The products and methods of the present invention satisfy the aforementioned need in the art by providing a radically different approach to the production of biomolecules which relies on plant cells that have a biology far removed from animal, fungal or bacterial cells. Plant cells are photoautotrophic cells which typically do not require an energy input. Moreover, plant cells typically require a minimal nutrient input in terms of number, quantity and cost. Thus, plant cells provide cost advantages over the more familiar animal, fungal and bacterial host cell environments. The products and methods of the invention are designed to amplify, and optionally improve the expression of, nucleic acids in the cells of a plant. The invention reals the advantage of lowered costs resulting from reduced host cell requirements for energy and nutrients.

The present invention provides novel plant polynucleotides specifying Amplification Promoting Sequences (APSs) which are active in plants to amplify an adjacent target nucleic acid. For target nucleic acids encoding an expressible product, the plant polynucleotides according to the invention may be capable of improving expression beyond expectations focused solely on copy number. Preferred APSs of the invention comprise A-T rich (preferably 80% or more) rDNA intergenic polynucleotide sequences or subsequences derived from (or based on) e.g., tobacco (Borisjuk et al., Plant Mol. Biol. 35:655–660 (1997); SEQ ID NO:1 and SEQ ID NO:2), L. esculentum (Perry et al., Mol. Gen. Genet. 221:102–112 (1990); SEQ ID NO:4), and S. tuberosum (Borisjuk et al., Plant Mol. Biol. 21:381–384 (1993); SEQ ID NO:3). Presently most preferred plant APSs comprise the N. tabacum-derived polynucleotide set out in SEQ ID NO:1 and plant polynucleotides which hybridize under stringent conditions to the complement of the sequence set forth in SEQ ID NO:1.

Also provided by the present invention are nucleotide segments comprising a plant APS and an adjacent target nucleic acid to be amplified, preferably located within the segment within 3000 nucleotides from the APS. Novel nucleotide segments of the invention may also comprise a plant APS and a homologous recombination locator polynucleotide functional to provide for site-specific insertion of the APS within another polynucleotide, e.g., a plant host chromosome or vector. Preferred novel nucleotide segments comprise vectors, including Agrobacterium-derived plant transformation vectors.

In another aspect of the invention, plants and plant host cells are provided which are stably transformed or transfected with plant-derived and non-plant derived APSs functional to amplify adjacent nucleic acids within the plants or plant cells. Such adjacent nucleic acids may be coding sequences (e.g., RNA and/or protein coding) or may be expression regulatory sequences. The present invention correspondingly provides novel methods for amplifying target nucleic acids within plants, which methods optionally include isolation of products coded thereby.

Yet another aspect of the invention is a method for enhancing mRNA expression of a target nucleic acid comprising the step of contacting a plant host cell under conditions suitable for transforming or transfecting the cell with an isolated polynucleotide specifying a plant-active Amplification Promoting Sequence (APS), the polynucleotide selected from the group consisting of a) a polynucleotide comprising the sequence set forth in SEQ ID NO:1 or a fragment thereof; and b) a polynucleotide which hybridizes to a polynucleotide having the complement of the sequence set forth in step a), the hybridization occurring in 3×SSC, 20 mM NaPO$_4$ (pH 6.8) at 65° C. with washing in 0.2×SSC at 65° C. The methods are particularly suited for the use of target nucleic acids that encode a polypetide; the methods may further comprise the step of recovering the expression product of said target nucleic acid. In addition, the isolated polynucleotide used in the methods may further comprise a promoter.

Numerous other aspects and advantages of the present invention will be apparent upon consideration of the following detailed description, including the drawing.

BRIEF DESCRIPTION OF THE DRAWING

FIG. 2 graphically illustrates expression cassette components of illustrative plasmids pNB35S-GFP-aps1 and pNB35S-GFP-aps2 according to the invention, together with experimental control plasmid pNB35S-GFP. Abbreviations: nos—nopaline synthase promoter; NPT II—neomycin phosphotransferase gene conferring resistance to the antibiotic kanamycin; ter- nos terminator; 2×En 35S—the Cauliflower Mosaic Virus 35S promoter with two enhancers; the TEV (i.e., tobacco etch virus) 5' nontranslated sequence (TL); GFP- Green Fluorescent Protein; and aps-amplification promoting sequence.

FIG. 6 provides data showing the number of plants (wild type or transformed with one of the constructs illustrated in FIG. 5) exhibiting root growth and visually normal development in the presence of the indicated amount of the herbicide Pursuit (American Cyanamid Co.)

DETAILED DESCRIPTION

Figure 1:
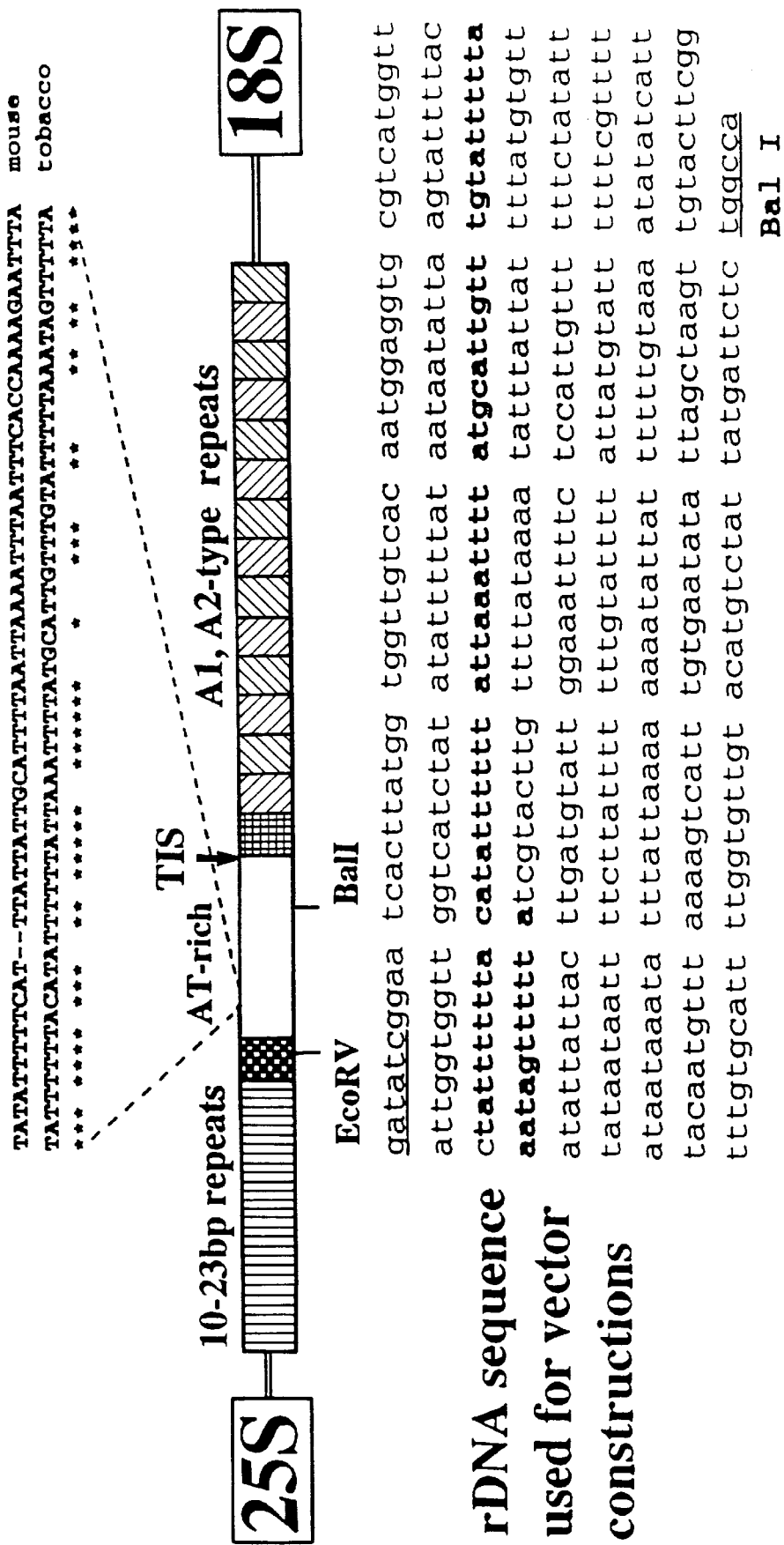
FIG. 1 provides a graphic representation of the intergenic region separating 25S and 18S rDNAs of N. tabacum. Specifically illustrated are the 446 nucleotides (SEQ ID NO: 1) spanning the intergenic region (SEQ ID NO:2) between EcoRV and BalI restriction sites along a subsequence (nucleotides 102 through 161 of SEQ ID NO: 1) compared to nucleotides 50 through 107 of M. muyculus rDNA muNTS1 sequence set out in Genbank Accession No. X52413; Wegner et al., Nucl. Acids Res. 17:9909–9932 (1989).

The products and methods of the invention provide the tools to increase the copy number of target nucleic acids in plant cells, thereby improving the expression of valuable biomolecules such as RNAs and proteins. In some embodiments of the invention, the methods result in expression improvements that exceed expectations based solely on the relative copy number of coding region targets. The following examples illustrate presently preferred embodiments of the invention. Example 1 describes the construction of recombinant polynucleotides for expression of Green Fluorescent Protein (GFP) in plants. Example 2 discloses the generation of transgenic plants by transformation with the recombinant polynucleotides of Example 1. Example 3 describes Southern, Northern, and protein expression analyses of samples from transgenic plants according to Example 2. Additionally, Example 4 provides a description of comparative Southern and Northern analyses of transgenic plants disclosed in Example 2.

EXAMPLE 1

Plasmids were constructed using standard recombinant DNA techniques. Sambrook et al., in Molecular Cloning, Cold Spring Harbor Laboratory Press, Cold Spring Harbor, N.Y. (1989). Two recombinant molecules according to the invention are pNB35S-GFP-aps1 and pNB35S-GFP-aps2. These recombinant molecules were independently derived from plasmid Nt4-19. Nt4-19, in turn, is a subelone of Nt-4, which contains the whole sequence of the tobacco ribosomal DNA, or rDNA, intergenic spacer (Borisjuk et al., plant md. Biol. 35:655–660 1997). To create Nt4-19, an EcoRV-HindIII fragment of the tobacco IGS sequence available from GenBank under Accession No. Y08422, containing the central AT-rich region of a tobacco intergenic space or IGS (including the transcription initiation site, TIS), was excised from Nt-4 and inserted into the SmaI and HindIII sites of plasmid pUC19. An EcoRI-BalI fragment homologous to the mouse muNTS1 (see, plant DNA sequence positions 1–446 shown in SEQ ID NO: 1) was then excised from Nt4-19 and ligated into the EcoRI and SmaI sites of the exemplary binary plant transformation vector pBin19, resulting in formation of plasmid pBin-aps.

Recombinant molecules for the expression of GFP were based on the plasmid pCK GFP S65C, a pUC derivative containing the mutated GFP DNA sequence under the control of the CaMV 35S promoter with two enhancers. Reichel et al., Proc. Natl. Acad. Sci. (USA) 93:5888–5893 (1996).

A GFP expression cassette derived from pCK GFP S65C and composed of the cauliflower mosaic virus 35S promoter with a duplication in the upstream regulatory sequence, the TEV 5' nontranslated sequence, the GFP sequence, and the cauliflower mosaic virus polyadenylation signal, was excised with HindIII and ligated into the dephosphorylated HindIII site of pBin-aps, creating pNB35S-GFP-aps1 and pNB35S-GFP-aps2. These two recombinant molecules differ from each other in the orientation of the expression cassette relative to the plant-active APS and NPTII (i.e., neomycin phosphotransferase coding region) elements. (See FIG. 2).

A control plasmid capable of expressing GFP from the CaMV 35S promoter, but lacking an APS, was constructed and designated pNB35S-GFP. This plasmid was generated by initially restricting pCK GFP S65C with HindIII, thereby excising a fragment containing the GFP coding region flanked, in proper orientation, by the CaMV 35S promoter (including two enhancer sequences and the TEV 5' nontranslated sequence) and a terminator sequence. The vector pBin19, containing the previously described NPTII selectable marker, was digested with HindIII. The GFP-containing fragment from pCK GFP S65C was then inserted into pBin19, thereby generating pNB35S-GFP. (See FIG. 2).

EXAMPLE 2

The recombinant molecules described in Example 1 were separately introduced into tobacco plants using *Agrobacterium tumefaciens*. The streptomycin resistant Agrobacterium strain LBA4404, used for plant transformation, was itself transformed with the corresponding recombinant molecules using a variation of the freeze-thaw procedure described by Hood et al., J. Bacteriol. 168:1291–1301 (1986). The transformed Agrobacteiium cells were prepared using a standard transformation protocol, followed by growth at 28° C. for 4048 hours in liquid YM medium containing streptomycin and kanamycin, each at 50 mg/L. One liter of YM medium contains 0.4 g yeast extract (autolyzed, low sodium); 10 g mannitol, 0.1 g NaCl, 0.2 g $MgSO_4$ and 0.5 g of $K_2HPO_4$. YM medium (Gibco BRL) is specifically formulated for the growth and expression of Agrobacterium. Transformation of *Agrobacterium tumefaciens* LBA4404 was confirmed by Southern DNA hybridization. Although *Agrobacterium tumefaciens* LBA4404 and recombinant molecules derived from pBin19 are preferred for use in practicing the present, invention, any of the conventionally known and available plant transformation vectors can be modified by introducing a plant-active APS sequence and used in conjunction with any suitable *Agrobacterium tumefaciens* strain in practicing the methods of the invention.

Transformation of tobacco plants (e.g., *Nicotiana tabacum* cv. Wisconsin and cv. Samsun NN) was effected by leaf-disk co-cultivation, as described by Weissbach et al., in Plant Molecular Biology-Technique (Academic Press, Inc. San Diego 1988). Healthy unblemished leaves were harvested from sterile young plants and cut into strips 5–10 mm wide. These explant tissues were infected by submersion in a suspension of transformed Agrobacteriwn cells. Following exposure to Agrobacterium, explant tissues were then blotted dry on sterile filter paper, inverted, placed on MS medium in tissue culture plates and incubated for a co-cultivation period of 36–48 hours. (MS medium is a conventional medium for the in vitro culture of plants, Murashige et al., Physiol. Plantarum 15:473–479 (1962)). Subsequently, explants were transferred to agar plates (8 g/L) containing regeneration medium (MS salts, 30 g/L sucrose, 1 mg/L BAP (i.e., 6-benzylaminopurine, a plant cytokinin), 500 mg/L of carbeniclilin to eliminate bacterial growth, and 100 mg/L of kanamycin as a selective agent for transgenic plants). Transformants were selected on the same medium without any hormone. Incubation was continued until roots had formed.

EXAMPLE 3

Copy numbers of specific DNAs in transgenic tobacco plants were determined by Southern blot analyses. Total genomic DNA was independently isolated from five transgenic plants containing pNB35S-GFP-aps1, five transgenic plants containing pNB35S-aps2, and two transgenic plants containing pNB35S-GFP. DNA isolations were performed using the Phytopure plant DNA extraction kit from Nucleon Biosciences according to the manufacturer's instructions. Following isolations, genomic DNAs were digested to completion with HindIII and equal quantities were fractionated by agarose gel electrophoresis using standard techniques. Fractionated DNAs were then transferred to HyBond-N+ membranes (Amersham Corp.) and exposed to a $^{32}$P-labeled probe (incorporated [$\alpha$-$^{32}$] dCTP) specific for the GFP coding region using a Southern hybridization protocol known in the art. Sambrook et al. (1989). Results were visualized using a Phospho-Imager SI System (Molecular Dynamics, Inc.) and the data were evaluated using proprietary Phospho-imager software. The results showed a 3–15 fold amplification of the GFP coding region when adjacent to the APS, relative to the GFP coding region levels in the absence of an adjacent APS.

The copy number of a target nucleic acid, such as GFP, situated adjacent an APS according to the invention was also assesed relative to a unique or single-copy calreticulin gene in tobacco cells. Borisjuk et al., Planta 206:504–514 (1998). Hybridization signals attributable to GFP and calreticulin polynucleotides were subjected to comparative Southern hybridizations, with individual filters separately being exposed to each of the two probes. Results were analyzed using ImageMaster Video System software (Pharmacia-Upjohn, Inc.) control plants without APS contain 1–2 copies of the introduced DNA, while 60% of GFP-APS transformants contain 3–40 copies of the introduced foreign sequences and the remaining contain 1–2 copies.

Production of specific mRNA levels in the transgenic tobacco plants was also determined. Northern blot analyses were performed using total RNA isolated from leaf tissues in accordance with the procedure of Chomczynski et al., Anal. Biochem. 162:156–159 (1987). 10 μg of isolated RNA were separated by denaturing 1.5% agarose gel electrophoresis, transferred onto Hybond N$^+$ membrane (Amersham Inc., Arlington Heights, Ill.) and hybridized to a $^{32}$P-dCTP labeled DNA fragment encoding GFP. The DNA fragment used as a hybridization probe was prepared by digestion of pCK-GFP-C65 with NcoI and XbaI followed by agarose gel fractionation and isolation of the DNA fragment encoding GFP. Hybridization was performed overnight at 65° C. according to the protocol of Church et al., Proc. Natl. Acad. Sci. (USA) 81:1991–1995 (1985), using HYPE buffer (1% BSA, 1 mM EDTA, 0.5M Na·P0$_4$ pH 7.2, 7% SDS) as a hybridization buffer. After hybridization, filters were washed twice for 5 minutes at 65° C. in wash buffer 1 (0.5% BSA, 1 mM EDTA, 0.04 M NaHPO$_4$ pH 7.2, 5% SDS), followed by four washes for 5 minutes each at 65° C. in wash buffer 2 (1 mM EDTA, 0.04 M NaBPO$_4$ pH 7.2, 1% SDS). Radioactive hybridization signals were detected with the Phospho-Imager SI System. Relative expression levels of GFP MRNA were quantified using the ImageQuanNT image analysis software package available from Molecular Dynamics, Inc. The quantification data showed a 2 to 20 fold stimulation of heterologous mRNA expression in transgenic plants containing the amplification promoting sequence from transformation plasmids pNB35S-GFP-aps1 and pNB35S-GFP-aps2, as compared to transgenic tobacco transformed with pNB35S-GFP. The relative increases of 2 to 20 fold in mRNA production may not be due solely to the copy number effect which resulted in a 3 to 15 fold amplification of specific DNAs.

The effect of an APS sequence on expression was also revealed by plating transformants on selective MS medium containing increasing concentrations of kanamycin and determining the frequency of surviving colonies. Cells from plants transformed with either of the APS-containing plasmids had enhanced survival characteristics, attributable to increased expression of the NPTII gene. These results indicate that an amplification of the NPTII gene had also occurred.

To show that the elevated mRNA levels in APS transformed plants were correlated with an increased synthesis of recombinant protein, GFP expression was measured using both fluorescent and immunological techniques. The unique bioluminescent feature of GFP (excitation at 475 nm; emission at 510 nm) were used to microscopically detect this protein in plant tissues. Plant roots, freshly prepared in 0.05 M Tris HCl pH 8.0, were irradiated in the long-UV range of the electromagnetic spectrum with a fluorescent microscope (Nikon, Inc) for an empirically optimized period of 30 seconds. Qualitative measurements showed that the roots of transgenic plants containing pNB35S-GFP-aps1 or pNB35S-GFP-aps2 fluoresced brightly, in contrast to the roots of transgenic plants containing the control plasmid pNB35S-GFP, which did not fluoresce.

For Western blot analysis, GFP was detected using anti-GFP monoclonal antibodies produced by mouse hybridoma cells (Clontech, Inc.) using the Western Exposure Chemiluminescent Detection System PT 1 600-1, available from the same supplier. Proteins extracted from the leaves were separated on 12% SDS-PAGE and electrophoretically transferred onto PVDF membranes using the Bio-Rad Mini-Protein system (100 V constant voltage at 4° C., 1.5 hours). Pre-stained low-molecular weight SDS-PAGE standards (Bio-Rad Laboratories, Inc.) were used as molecular weight markers. Primary antibodies were diluted 1:500 and the secondary antibody—phosphatase conjugate was diluted 1:15,000. A single sharp protein band corresponding to the expected size of 27 kDa was detected.

The quantification of recombinant protein in leaf extracts was also performed by indirect enzyme-linked immunosorbent assay (EBLISA) using polyclonal antibodies to GFP as primary antibodies and horseradish peroxidase (EC. 1.11.1.7) labeled antibodies as secondary antibodies. ABTS (2,2'-azino-bis (3-ethylbenzthiazoline)-6-sulfonic acid) was used as substrate for the peroxidase in the colorimetric detection reaction. Optical density was determined spectrophotometrically at 405 nm using a PERKIN-ELMER Spectrofluorimeter LF-50B. The ELISA data showed 3 to 30 times higher amounts of GFP expressed from pNB35S-GFP-aps1 and pNB35S-GFP-aps2 plants as compared to the GFP expression levels in pNB35SGFP plants. These results establish a positive correlation between GFP mRNA levels and GPP protein levels in transgenic plants expressing heterologous genes adjacent to an APS.

EXAMPLE 4

Figure 3A:
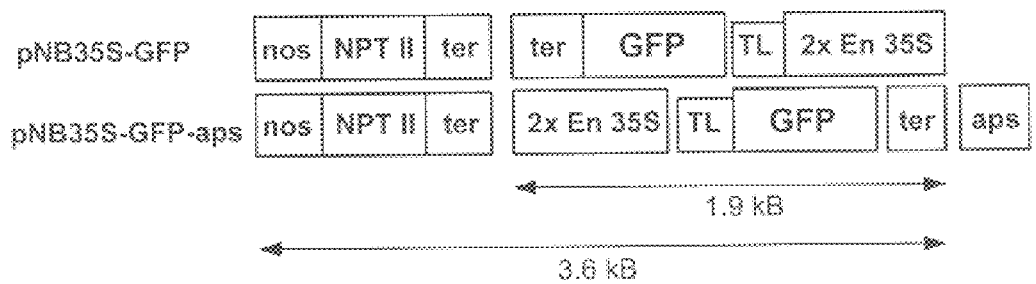
FIG. 3A illustrates expression cassette components of plasmids pNB35S-GFP-aps1 and pNB35S-GFP.
Figure 3B:
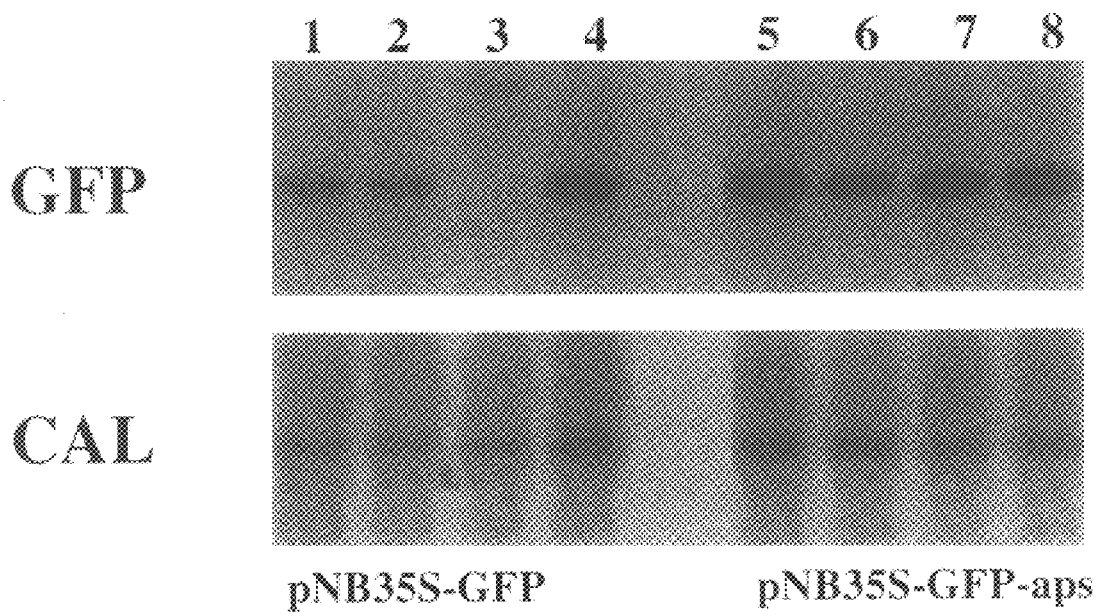
FIG. 3B presents the autoradiographic data of Southern analyses of several independent transgenic tobacco plants transformed either with pNB35S-GFP-aps1 or the control, pNB35S-GFP, using either a GFP-specific probe (upper panel) or a calieticulin-specific probe (lower panel).
Figure 3C:
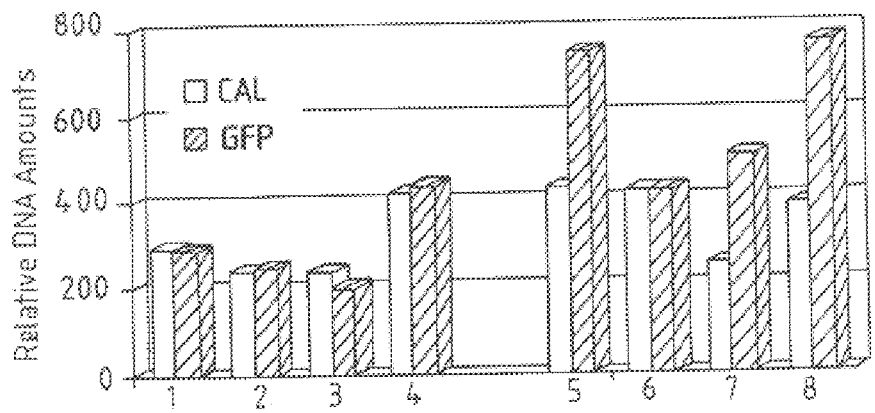
FIG. 3C graphically shows the quantification of the data shown in FIG. 3B.

A group of transgenic pNB35S-GFP-aps1 tobacco plants was analyzed to determine the number of introduced expression cassettes by comparative Southern hybridizations with the GFP probe and the cDNA coding for calreticulin as an internal DNA standard. Analyses were performed using total genomic DNA separately isolated from each one of 49 pNB35S-GFP-asp1 or pNB35S-aps2 plants and nine pNB35S-GFP plants using the "Phytopure plant DNA extraction" kit Nucleon Biosciences). Isolated DNAs were individually digested to completion with HindIII and the DNA fragments were separated by agarose gel electrophoresis. Following electrophoretic fractionation, the DNA fragments were transferred to Hybond-N$^+$ membrane (Amersham Corp.) using a conventional protocol. Immobilized DNA fragments were then hybridized to $^{32}$P-labeled probes (i.e., DNA fragments) specific for one of GFP, NPTII or calreticulin. cDNA coding for the tobacco endoplasmic reticulum protein calreticulin was used as an internal DNA standard because it has been shown to be a single copy sequence in the tobacco genome (Borisjuk et al., Planta 206:504–514 (1998)). To control for variation in DNA amounts subjected to analysis, a single membrane containing the DNA of an individual plant was probed with both the GFP-specific probe and the calreticulin-specific control probe. DNA hybridizations and removal of bound probes were conducted according to the supplier's (Amersham Corp.) recommendations. Membranes were exposed to X-ray film and images were quantitated using ImageMaster VDS software (Pharmacia-Upjohn, Inc.) and graphically plotted using Axum (v. 5) software. The calreticulin signal was used to provide a baseline for determining the relative GFP hybridization signals for each plant. The lowest GFP signal was defined as 1 copy of the inserted expression cassette per genome. The data is presented in FIG. 3, wherein FIG. 3A shows the results of Southern hybridizations of DNAs isolated from four independent pNB35S-GFP-transformed plant lines (lines 1–4) and pNB35S-GFP-asp1 (lines 5–8) plants. The plant lines were numbered to correspond to the gel lane in which their DNAs are displayed in FIG. 3A. Immobilized DNAs were probed with GFP-specific probe (upper panel) and a calreticulin-specific probe (bottom panel). The same filter was hybridized to $^{32}$-labeled GFP probe, stripped, and hybridized to the calreticulin-specific probe. FIG. 3B graphically shows the Southern results described above. Approximately equal relative intensities of calreticulin and GFP hybridizations in pNB35S-GFP plants (lines 1–4) and in line 6 of pNB35S-GFP-asp1 plants indicates that each plant contained a single copy of the GFP expression cassette. GFP hybridization signals two-fold more intense than the calreticulin signal in pNB35S-GFP-asp1 lines 5, 7 and 8 showed that these lines contain two copies of the GFP expression cassette per genome. As shown in FIG. 3, control plants (i.e., transgenic plants lacking an introduced APS) were found to contain 1–2 copies of the GFP coding region, while 60% of the GFP-APS transformants contained 3–40 copies the GFP coding region. The remaining 40% of the GFP-APS transformants contained 1–2 copies of the GFP coding region.

GFP transcription in all of the GFP-APS transgenic plants was also investigated. Total RNA was isolated from leaf tissues using the procedure of Chomczynski et al. (1987). Ten $\mu$g of isolated RNA from each plant were then fractionated on a denaturing 1.5% agarose gel. Fractionated RNAs were then transferred to Hybond N$^+$ membrane (Amersham Corp.) and hybridized to $^{32}$P-labeled DNA fragments coding for either GFP or NPTII. Hybridization was performed overnight at 65° C. according to Church et al. (1984), using Hype buffer (1% BSA, 1 mM EDTA, 0.5 M NaHPO$_4$ pH 7.2, 7% SDS) as a hybridization medium. After hybridization, filters were washed twice for 5 minutes each at 65° C. in wash buffer 1 (0.5% BSA, 1 mM EDTA, 0.04 M NaHPO$_4$, pH 7.2, 5% SDS), four times for 5 minutes each at 65° C. in wash buffer 2 (1 mM EDTA, 0.04 M NaHPO$_4$ pH 7.2, 1% SDS) and exposed to X-ray film. Relative expression levels of GFP mRNA were again quantified using ImageMaster VDS software.

Figure 4A:
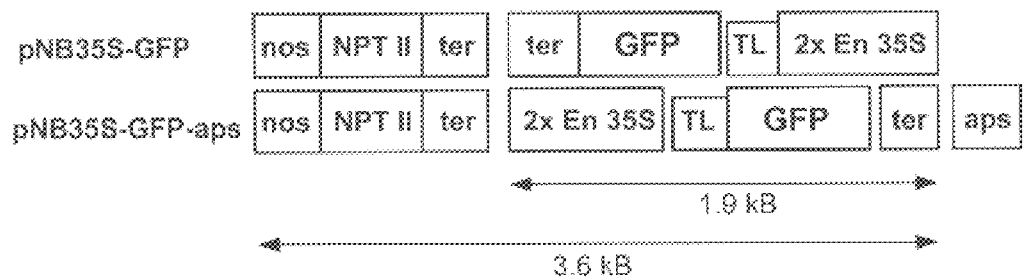
FIG. 4A shows expression cassette components of plasmids pNB35S-GFP-aps1 and pNB35S-GFP.
Figure 4B:
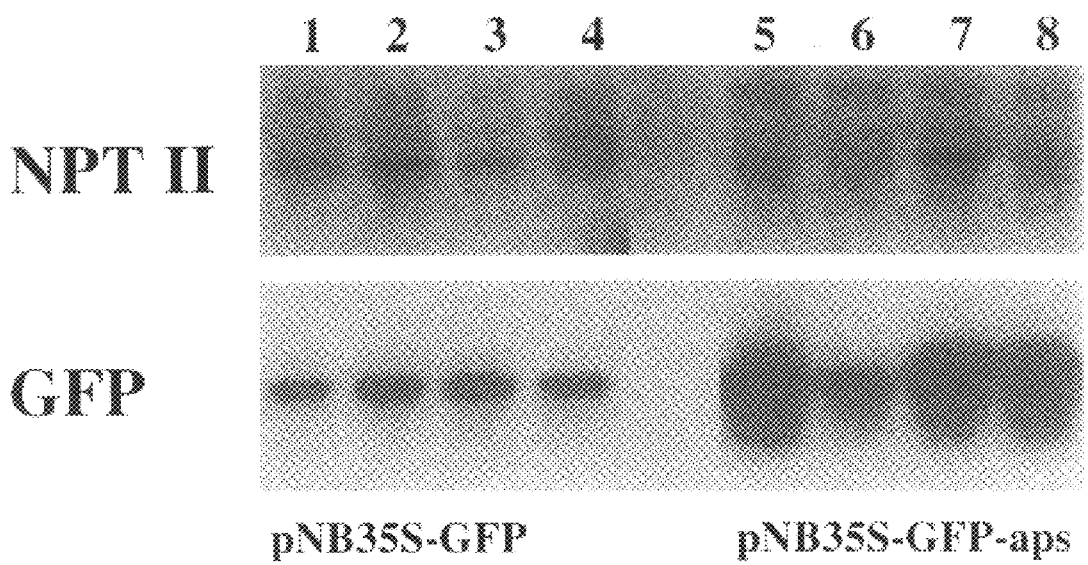
FIG. 4B presents the results of Northern hybridizations involving RNA from transformed tobacco plants interrogated with an NPTII-specific probe (upper panel) or a GFP-specific probe (lower panel).
Figure 4C:
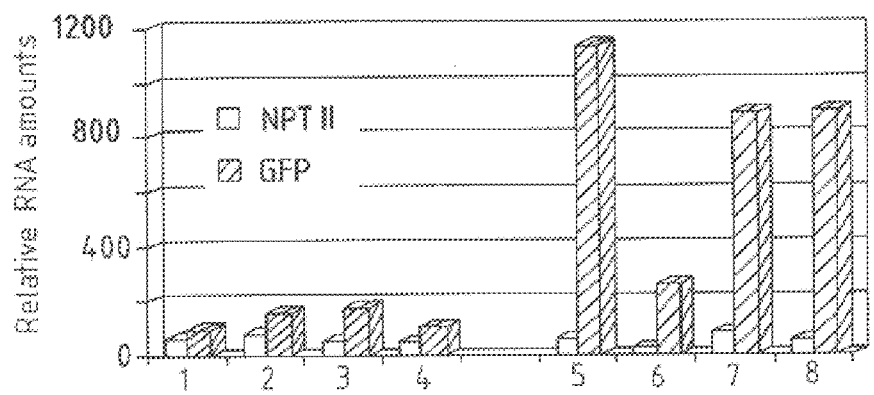
FIG. 4C presents a quantification of the data shown in FIG. 4B in graphic form.

The data presented in FIGS. 4A and 4B show the stimulation or enhancement of GFP mRNA expression in transgenic plants containing the APS, as compared to transgenic plants containing the same expression cassette without an APS. In particular, FIG. 4A shows the results of Northern hybridizations of RNA isolated from pNB35S-GFP (lines 1–4) and pNB35S-GFP-asp1 (lines 5–8) plants. The lower panel of FIG. 4A presents the results of probing the immobilized RNAs (10 $\mu$g per lane) with a GFP-specific probe; the upper panel provides the results of probing those same RNAs with an NPTII-specific probe. FIG. 4B graphically quantifies the data shown in FIG. 4A. Of note is the observation that GFP transcription was elevated in all plants transformed with pNB35S-GFP-asp1, including those plants containing 1–2 copies of the GFP coding region (see above). In general, plants transformed with vectors containing the APS sequence, pNB35S-GFP-asp1, had 2–5 fold more GFP mRNA than plants transformed with pNB35S-GFP, and therefore lacking an introduced APS. This observation holds true regardless of the relative copy number of the express-ible target such as GFP. The transcription levels of an NPT II gene, situated in the same expression cassette but farther from the APS element, were approximately the same in both pNB35S-GFP-asp1 and pNB35S-GFP plants (FIGS. 2B and 2C). The difference in transcription levels of the NPTII and GFP mRNAs in pNB35S-GFP plants is consistent with the relative strengths of the nopaline synthase (nos) promoter and the Cauliflower mosaic virus 35S (2En×35S) promoter with enhancers.

Figure 5:
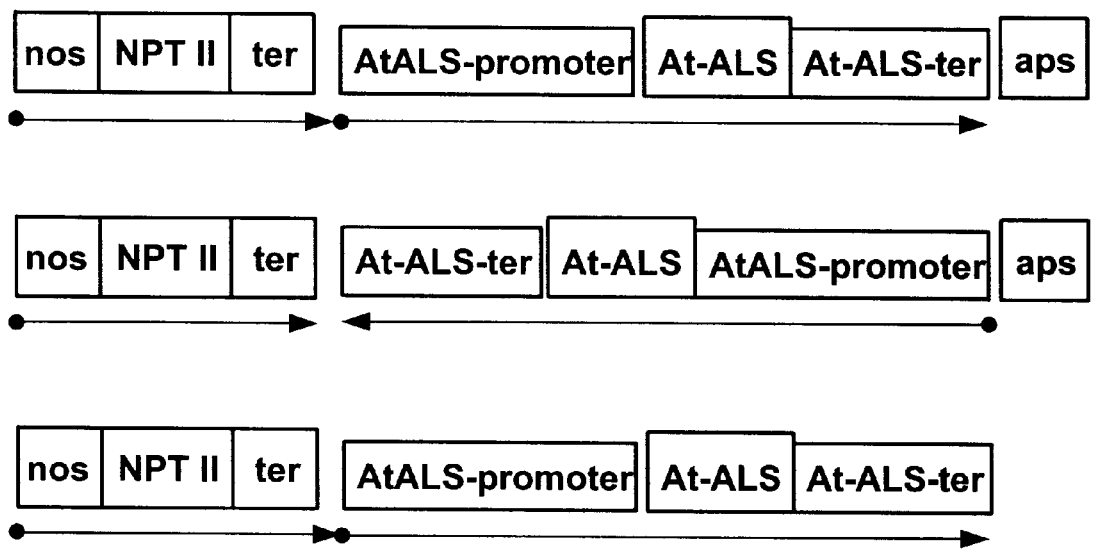
FIG. 5 schematically illustrates expression cassettes including the A. thaliana acetolactate synthase promoter and coding region in the presence, or absence, of an APS. The selectable NPTII marker expression unit is also shown.

Results of the comparative Southerns and Northerns described above in the context of GFP were essentially reproduced with a plant transgene and an animal virus transgene, each transgene having been introduced into tobacco plants as described above. The plant transgene was the acetolactate synthase (ALS) gene from *Arabidopsis thaliana* encoding an ALS that substituted serine for asparagine at position 653. Sathasivan et al., Nucl. Acids Res. 18:2188 (1990). The polynucleotide constructs used to introduce the ALS gene into tobacco are schematically shown in FIG. 5, which reveals that the ALS gene and the ALS promoter were cloned in both orientations relative to the tobacco APS (pNB-ALS-asp1 and pNB-ALS-aps2); a control construct lacked the APS entirely (pNB-ALS). Because ALS had been shown to confer some resistance to sulfonylurea herbicides such as chlorsulfuron (Haughn et al., Mol. Gen. Genet. 211:266–271 (1988)), the transgenic tobacco plants were challenged with Pursuit (American Cyanamid Co.), a commercially available herbicide in the sulfonylurea class. Following transformation of tobacco plants as described in Example 2, plants were grown for 3–4 weeks in MS medium supplemented with 1 $\mu$M herbicide. At this point, rootless explants were prepared and incubated in MS medium containing higher levels of the herbicide, as indicated in FIG. 6. The results presented in FIG. 6 indicate both the number of plants exhibiting root growth and normal development (i.e., healthy development based on gross visual examination) at each concentration of herbicide, as well as the percentage of plants rooting and growing normally relative to the plants able to grow and root in 1 $\mu$M herbicide. Results for plants transformed with either pNB-ALS-asp1 or pNB-ALS-aps2 were comparable and, hence, are presented collectively in FIG. 6. Apparent from the data in the Figure is the ability of plants transformed with either pNB-ALS-asp1 or pNB-ALS-aps2 to survive and thrive in herbicide concentrations extending up to at least 20 $\mu$M Pursuit. Plants transformed with pNB-ALS fail to show appreciable resistance to herbicide concentrations higher than 1 $\mu$M, consistent with the report of Haughn et al.

The animal gene used to transform tobacco plants was the Hepatitis B surface antigen (HBsAg). The relevant polynucleotide constructs resembled the GFP constructs described in Example 1, with the HBsAg coding region substituted for the GFP coding region. Tobacco plants transformed with a construct placing HBsAg under the control of the CaMV 35S promoter and an APS showed significant HBsAg transcription, as revealed by Northern hybridizations, and significant expression of HBsAg, as revealed by immunoassay.

These results indicate that the APS of the invention stimulates, or enhances, transcription of nearby coding regions. As used herein, "stimulates transcription" or "enhances transcription" means an increase in the level of transcripts, typically, but not necessarily, through an increased rate of transcription. Therefore, the Amplification Promoting Sequence, APS, elevates expression levels by both increasing coding DNA copy number and by directly influencing the transcriptional activity of those DNAs.

The preceding illustrative examples provide presently preferred embodiments of the invention which are clearly non-limiting on practice of the invention.

Thus, while the illustrative examples employ an APS comprising 446 nucleotides which is an exact replica of a sequence within an rDNA intergenic region of N. tabacum, the invention is not limited to use of such a sequence. Novel isolated APS polynucleotides may also be derived from other plant species, especially those wherein rDNA intergenic regions are revealed as including A-T rich sequences. As noted in Borisjuk et al. (1997), similar A-T rich regions are found in L. esculentum (see SEQ ID NO:4), S. tuberosum (see SEQ ID NO:3) and several other plants and are expected to be equally suitable for practice of the invention. Moreover, by analogy to development of "consensus" expression regulatory sequences based on regulatory sequences of multiple protein genes, it is expected that synthetic "consensus" plant APSs can be developed based on the A-T rich rDNA intergenic regions of several different plants.

Moreover, novel transformation methods and transformed plant cells and plants of the invention are not limited to incorporation of APSs derived from (or predominantly based on) plants and can involve use of "plant active" APSs derived from non-plant sources. The substantial sequence homology between a portion of the N. tabacum rDNA intergenic sequence and a portion of mouse muNTS1 sequence revealed in FIG. 1 indicates that all or part of the 370 base pair muNTS1 mouse APS, and other eukaryotic APS sequences, can be active to amplify adjacent target sequences in plants.

While an exemplary APS according to the invention has the 446 base sequence set forth in SEQ ID NO: 1, plant functional APSs are expected to exhibit a range of lengths. Given the functional (i.e., amplification and/or enhancement of transcription) characteristic of an APS according to the invention, determination of a minimum, maximum and/or optimum APS length is within the skill in the art, involving no more than routine optimization of a known parameter. For example, the skilled artisan can readily synthesize fragments or generate terminal deletions of cloned sequences in a processive manner to localize a sequence having APS activity; similarly, one of ordinary skill could create point or cluster polymorphisms to determine the need for internal nucleotides in an APS sequence capable of promoting amplification.

The invention thus comprehends novel isolated plant APSs having a sequence that hybridizes under stringent conditions to an APS having the complement of the sequence set forth in SEQ ID NO: 1. Exemplary stringent hybridization conditions include hybridization at 65° C. in 3×SSC, 20mM NaPO$_4$ (pH 6.8) and washing at 65° C. in 0.2×SSC. It is understood by those of skill in the art that variation in these conditions occurs based on the length and GC base content of the sequences to be hybridized. Formulas standard in the art are appropriate for determining exact hybridiztion conditions. See Sambrook et al., §§9.47–9.51 (1989).

A target nucleic acid may comprise a protein coding region (such as the GFP, NPTII, ALS, and HBsAg sequences exemplified above) or a regulatory domain. These target nucleic acids also may be homologous or heterologous to host nucleic acids depending on the plant host cell. The suitability of a given target nucleic acid length is readily determinable by assessing whether an APS is capable of amplifying and/or enhancing the transcription of that target nucleic acid, using the disclosures provided herein. Such assessments are routine for those of ordinary skill in the art.

To amplify a target nucleic acid, a polynucleotide specifying an APS is placed adjacent to the target nucleic acid, i.e., located on the same nucleic acid molecule as the target. Thus, "adjacent" as used herein does not mean that the APS and the target nucleic acid must exhibit a direct physical connection or requisite 3' or 5' orientation. In analogous constructs, for example, entire vectors containing, e.g., a muNTS1 sequence have been amplified in mammalian cells, indicating that a separation of several kb does not prevent a mammalian APS from amplifying a target nucleotide sequence. Hemann et al. (1994). Although several kb may separate an APS from a target, it is preferred that the APS be found within 3 kb of the target nucleic acid. Again, suitable maximum or optimum separations between an APS and a target nucleic acid may be determined by the skilled artisan using conventional techniques in routine experiments. It is generally expected that the closer an APS and a target nucleic acid are located, the greater the likelihood that the APS will be active in promoting the amplification of the target.

Amplification of the target nucleic acid is designed to affect the physiology of the host cell in a desirable way. For example, a target nucleic acid comprising a regulutory signal may provide a binding site for a regulatory polypeptide. Amplification of the binding site would titrate out the regulator, thereby altering the expression of the regulated genes, such as genes encoding commercially valuable gene products. Alternatively, the target nucleic acid may itself encode a valuable gene product such as a polypeptide useful in medical diagnostics or therapeutics.

The invention also contemplates nucleotide segments wherein an APS is placed adjacent to at least one (flanking) homologous recombination locator nucleotide sequence that is similar to a region adjacent a target nucleic acid sequence with a level of similarity sufficient to allow for insertional homologous recombination to occur in a location close enough to permit the APS to promote the amplification of the target.

Vectors according to the invention may contain any of the foregoing nucleic acid molecules or constructs. Suitable vectors include plasmid, viral, and plasmid/viral (e.g., phagernid) hybrid vectors, as well as unmodified chromosomes and modified chromosomal vectors such as YACs. These vectors facilitate the stable introduction of at least one APS into a host plant cell. The vectors may also contain expression control elements such as promoters, enhancers, or sequences that facilitate translation initiation, as would be understood in the art.

Host cells according to the invention may be derived from a wide variety of sexually or vegetatively propagated plants, as well as intact living plant portions such as excised leaves, stems, roots, flowers, and tissues. Preferred for use in the methods of the invention are the cells of plant species representing different plant families such as tobacco (e.g., N. tabacum), tomato (e.g., L. esculentum), potato (e.g., S. tuberosum), and weeds (e.g., A. thaliana; see Grundler et al., J. Mol. Biol. 221:1209–1221 (1991)). In addition to these and other dicot exemplars, the invention contemplates monocot plants such as the grasses. Further, a plant of the present invention may be a mature plant or an immature plant such as a seedling. Preferred plants are capable of being sustained without organic nutrient supplementation and do not require sterile conditions.

Another aspect of the invention is directed to methods for amplifying a target nucleic acid within plant cells. The methods include a step for contacting a polynucleotide specifying an APS with a plant host cell. Following the contacting step, the methods according to the invention require minimal operator intervention. In some embodiments, the introduced nucleic acid molecules will affect host cell physiology without additional intervention. In other embodiments, the introduced nucleic acid molecules affect the copy number of a target nucleic acid, with either a direct or indirect effect on the expression of an encoded polypeptide. In these embodiments, the produced polypeptide may be recovered, using conventional cell culture and protein recovery techniques. Alternatively, the plant host cells may be subjected to regeneration protocols to produce intact plants expressing the polypeptide of interest. These plants may then be subjected to invasive or non-invasive recovery techniques known in the art.

Beyond the traditional use of Agrobactetium-based transformation protocols to transform dicots (see Example 2), it has been shown that Agrobactenum-based methods may also be employed to transfer heterologous (i.e., non-native) nucleic acids to monocot species in the generation of transgenic plants for use in methods according to the invention. Vain et al., Biotech. Advances 13:653–671 (1995), incorporated herein by reference.

Other transformation methodologies may also be employed to generate transgenic plants. For example, direct DNA transfer into plant cell protoplasts may be effected by the conventional techniques of calcium phosphate co-precipitation, the use of poly-L-ornithine, liposome-mediated transformation, electroporation, microinjection or fusagen-mediated (e.g., polyethylene glycol) transformation, and plants regenerated from the transformed protoplasts. PCT/US84/00050 and Christou, Euphytica. 85: 13–27(1995), each incorporated herein by reference. Other transfer methodologies such as biolistic transformation (i.e., microprojectile or particle bombardment) do not require plant cell protoplasts, thereby simplifying the process of regenerating transgenic plants. Consequently, biolistic transformation may be employed to introduce the coding region of a heterologous polypeptide, operatively linked to an APS, into a wide variety of plants, including both monocots and dicots. Christou (1995); Jahne et al., Euphytica 85:35–44 (1995), incorporated herein by reference.

Regeneration of transgenic plants from transformed cells, including transformed protoplasts, may be accomplished using any one of several techniques known in the art. Several approaches to the regeneration of transgenic plants are disclosed in EP-A-0 243 553, incorporated herein by reference. These approaches include regeneration via embryogenic or organogenic routes. Alternatively, plants may be regenerated following transformation by a method that incorporates a step for inducing meristem reorganization to increase the probability of obtaining transgenic germ cells, followed by a step providing conditions promoting differentiation of the meristem. PCT/US95/08977, incorporated herein by reference. In general, any of the transformation and regeneration methodologies known in the art may be used to generate transgenic plants for use in methods according to the invention. Alternatively, plant host cells transformed with a polynucleotide according to the invention may be maintained in culture using conventional techniques, rather than subjecting such cells to regeneration regimens to generate transgenic plants. Regenerated transgenic plants then may be subjected to conventional nucleic acid and/or polypeptide recovery techniques in accordance with methods of the invention.

Another aspect of the invention is methods of stimulating or enhancing the transcription of target nucleic acids by using an APS according to the invention. In some embodiments, the increased transcription is directly conelated with increased gene product expression. A variety of polynucleotides may be used in methods for enhancing the transcription of a target nucleic acid. Preferred polynucleotides include an APS, a coding region, and a functional promoter. The promoter may be the natural promoter for the coding region or a heterologous promoter element. Heterologous promoters may be derived from genes of the plant host other than the gene serving as a target, from other plants, from animals, from eukaryotic or prokaryotic viruses, or from chemical syntheses. All types of promoters are contemplated by the invention, including eukaryotic types I, II, and III promoters, prokaryotic promoters, viral promoters, and chimeras thereof. In preferred embodiments of the invention, a promoter for inclusion in a polynucleotide and for use in a method for enhancing transcription may be selected from the group consisting of eukaryotic types II and III promoters, prokaryotic promoters, viral promoters, and chimeras thereof. Also preferred are eukaryotic type II promoters, which are expected to be useful, e.g., in methods for enhancing the transcription of targets that are eukaryotic structural genes. Of course, the methods for enhancing transcription may additionally involve other expression control elements and/or signals known in the art.

Any of the wide variety of targets identified above also may be used in the methods for enhancing transcription. As in the case of amplification methods according to the invention, the APS may be placed in either orientation relative to the target coding region in practicing the methods for enhancing transcription. Moreover, the APS may be located upstream or downstream from the target nucleic acid. In addition, the APS may be located at some distance from the target, but is preferably located within 3,000 bp and, more preferably, within about 2,000 bp, such as 1,900 bp. Also, suitable plant host cells for practicing the methods for enhancing transcription have been defined above; a preferred plant host cell is a tobacco cell.

While the present invention has been described in terms of specific embodiments, it is understood that variations and modifications will occur to those skilled in the art. Accordingly, only such limitations as appear in the appended claims should be placed upon the invention.

What is claimed is:

1. A method for increasing the copy number of a target nucleic acid comprising the step of contacting a plant host cell under conditions suitable for transforming or transfecting said cell with an isolated polynucleotide comprising a plant-active Amplification Promoting Sequence (APS), said polynucleotide selected from the group consisting of:
   a) a polynucleotide comprising the sequence set forth in SEQ ID NO:1 or a fragment thereof; and
   b) a polynucleotide which hybridizes to a polynucleotide having the complement of the sequence set forth in step a), said hybridization occurring in 3×SSC, 20 mM NaPO$_4$ (pH 6.8) at 65° C. with washing in 0.2×SSC at 65° C.; wherein said target nucleic acid is located within the genome of said plant host cell or is operably linked to the APS, and wherein said host cell has a greater copy number of the target nucleic acid compared to the copy number in cells in which the APS has not been introduced.

2. The method according to claim 1 wherein said target nucleic acid is operably linked to the APS.

3. The method according to claim 2 wherein the target nucleic acid comprises a coding region.

4. The method according to claim 3 further comprising the step of recovering the expression product of said target nucleic acid.

5. The method according to claim 1 wherein said isolated polynucleotide further comprises a homologous recombination locator polynucleotide.

6. A recombinant polynucleotide segment specifying an Amplification Promoting Sequence (APS) that is active in plants to amplify the copy number of a target nucleic acid, said segment comprising:
   a) an APS selected from the group consisting of a polynucleotide comprising the sequence set forth in SEQ ID NO:1 or a fragment thereof, and a plant-derived polynucleotide which hybridizes to a polynucleotide having the complement thereof, said hybridization occurring in 3×SSC, 20 mM NaPO$_4$ (pH 6.8) at 65° C. with washing in 0.2×SSC at 65° C.; and
   b) a polynucleotide selected from the group consisting of an animal or non-rDNA plant target nucleic acid and an animal or non-rDNA plant homologous recombination locator polynucleotide.

7. The polynucleotide segment according to claim 6, wherein said plant-active APS comprises an rDNA intergenic sequence.

8. The polynucleotide segment according to claim 7 wherein said rDNA intergenic sequence is derived from a plant selected from the group consisting of *N. tabacum, L. esculentun* and *S. tuberosum*.

9. The polynucleotide segment according to claim 8 wherein said APS is within about 3,000 nucleotides of said target nucleic acid.

10. An expression cassette comprising the polynucleotide segment according to claim 6.

11. A vector comprising the polynucleotide segment according to claim 6.

12. A plant host cell transformed or transfected with the polynucleotide segment according to claim 6.

13. A recombinant polynucleotide segment specifying an Amplification Promoting Sequence (APS) that is active in plants to amplify the copy number of a target nucleic acid, said segment comprising:
    a) an APS selected from the group consisting of a polynucleotide comprising the sequence set forth at nucleotides 101 to 161 in SEQ ID NO:1 or a fragment thereof, and a plant-derived polynucleotide which hybridizes to a polynucleotide having the complement thereof, said hybridization occurring in 3×SSC, 20 mM NaPO$_4$ (pH 6.8) at 65° C. with washing in 0.2×SSC at 65° C.; and
    b) a polynucleotide selected from the group consisting of an animal or non-rDNA plant target nucleic acid and an animal or non-rDNA plant homologous recombination locator polynucleotide.

14. A method for enhancing mRNA expression of a target nucleic acid comprising the step of contacting a plant host cell under conditions suitable for transforming or transfecting said cell with an isolated polynucleotide comprising a plant-active Amplification Promoting Sequence (APS), said polynucleotide selected from the group consisting of:
    a) a polynucleotide comprising the sequence set forth in SEQ ID NO:1 or a fragment thereof; and
    b) a polynucleotide which hybridizes to a polynucleotide having the complement of the sequence set forth in step a), said hybridization occurring in 3×SSC, 20 mM NaPO$_4$ (pH 6.8) at 65° C. with washing in 0.2×SSC at 65° C.; wherein said target nucleic acid is located within the genome of said plant host cell or is operably linked to the APS, and wherein said host cell has a greater copy number of the target nucleic acid compared to the copy number in cells in which the APS has not been introduced.

15. The method according to claim 14 wherein said target nucleic acid encodes a polypeptide.

16. The method according to claim 14 wherein said isolated polynucleotide further comprises a promoter.

17. The method according to claim 14 further comprising the step of recovering the expression product of said target nucleic acid.

* * * * *

SEQUENCE LISTING

<160> NUMBER OF SEQ ID NOS: 4

<210> SEQ ID NO 1
<211> LENGTH: 446

```
<212> TYPE: DNA
<213> ORGANISM: Nicotiana tabacum

<400> SEQUENCE: 1
gatatcggaa tcacttatgg tggttgtcac aatggaggtg cgtcatggtt attggtggtt      60
ggtcatctat atatttttat aataatatta agtattttac ctattttta catatttttt     120 attaaatttt atgcattgtt tgtattttta aatagttttt atcgtacttg ttttataaaa     180
tatttattat tttatgtgtt atattattac ttgatgtatt ggaaattttc tccattgttt     240
tttctatatt tataataatt ttcttatttt tttgtatttt attatgtatt ttttcgtttt     300
ataataaata tttattaaaa aaatattat tttttgtaaa atatatcatt tacaatgttt      360
aaaagtcatt tgtgaatata ttagctaagt tgtacttcgg tttgtgcatt ttggtgttgt     420
acatgtctat tatgattctc tggcca                                          446

<210> SEQ ID NO 2
<211> LENGTH: 5140
<212> TYPE: DNA
<213> ORGANISM: Nicotiana tabacum
<220> FEATURE:
<221> NAME/KEY: misc_feature
<222> LOCATION: (1)..(5140)
<223> OTHER INFORMATION: intergenic spacer between 25S and 18S rRNA
      genes
<220> FEATURE:
<221> NAME/KEY: misc_feature
<222> LOCATION: (1703)..(2144)
<223> OTHER INFORMATION: AT-rich region

<400> SEQUENCE: 2 cctccccct ccattcaatc aatttataac tctttcgaaa agaggtttat tccttccttg       60
atgctatatt atatgccagt gttggaaatc gaacaagtcc tcaataccat ggaacgtatt    120
ctatttgtgt attagtataa tgtgacttgt cacttagtcg tttgtgggaa aggcttgcct    180
atgacgctaa acccaactta acttatagag gttttcgag gtgtcgtgtg cgatgccaag     240
gcacaagcaa gaatgatgtg ccaaggcacg agacgtcgga cgctgcggga catggcacgg    300
cgtcggacgt ggccatggca cggcgtcgga cgttgcccat ggccaagcgt cggacgtggt    360
aggacatggc catcgcacga cataggacat gatgggacat gcagggcttg gccatggca    420 cattcatcgg acgtggtatt acatggccat cgcacgacgt aggacatagt gggacatagc    480
acggttggtc gtacgtggca ggacatgacc atgcaggac atggcaggac gcaggacatg     540
gcagggcttg gccatggctc ggcgtcggac gggccatggc tcggctcgt acgtggaagg    600 acatggccat gacacgagca gggcgtggcc atgcacgac atcggacgtc tcatggcacg    660
gcgtcggacg tcgcaggaca tgaccatggc acgacgcagg acatgacagg acgtggccac    720
gccaggacgc aggacatggc aggacgcagg acatggcagg gcgtggccat ggctcggcgt    780
cggacgtgga aggacatggc catggtacga cgcagggcat ggcagggcgt ggccatggca    840
cggtgtcgga cgtggtagga tatggccatg gcacgacgca ggacatgacg ggacatggca    900
ggacgcagga catggcaggg cgtggctatg gcccgacgca ggacgtgtcg gacgtggcag    960
gacatggcca tggcacgacg caggacatga caggacatgg ccacggcagg acgcaggaca   1020
tggcaggacg caggacatgg cagggcgtgg ccatggctcg gcgtcggaca tggccatggc   1080
tcggcatcgg acgtggaagg acatggcgat ggcacgacgc agggcgtggc catggcacgg   1140
catcggacgt ctcatggcac ggcgtcggac gtcgcaggac atggacatgg caggacgcag   1200
gacatggcag gacgtggcca cggcaggacg caggacatgg caggacgcag gacatggcag   1260
```

```
ggcgtggcca tggctcggcg tcggacgtgg ccatggctcg gcgtcggacg tggaaggaca   1320
tggccatggc acgacgcagg gcgtgtccat ggcacggcat cggacgtctc atggcacggc   1380
gtcgggatgt ggcaggacat ggccatggca caacgcagga catgacagga catggccacg   1440
gcaggacgca ggacatggca gggcgtggcc atggcacgac gtcgcaccac gtcgcaccat   1500
atctagtgct agccaatgtt taacaagatg tcaagcacaa tgaatgttgg tggttggtgg   1560
tcgtggctgg cggtggtgga aaattgcgt ggttcgagcg gtagtgatcg gcgatggttg   1620
gtgtttgcag cggtgtttga tatcggaatc acttatggtg gttgtcacaa tggaggtgcg   1680
tcatggttat tggtggttgg tcatctatat attttttataa taatattatg tattttacct   1740 atttttaca tattttttat taaattttat gcattgtttg tatttttaaa tagtttttat   1800
cgtacttgtt ttataaaata tttattattt tatgtgttat attattactt gatgtattgg   1860
aaattttctc cattgttttt tctatattta taataatttt cttattttt tgtattttat   1920 tatgtatttt ttcgttttat aataaatatt tattaaaaa atattattt tttgtaaaat   1980 atatcattta caatgtttaa aagtcatttg tgaatatatt agctaagttg tacttcggtt   2040
tgtgcatttt ggtgttgtac atgtctatta tgattctctg gccaaaacat gtctactcct   2100
gtcacttggg tttttttttt taagacatat ataaggggg tagaggtgtt gaaaggcacc   2160
tcaaggtgct tgctgcctgg ccgaggcggg catggcacgg gggacgctgg catgcggcgt   2220
gggcattggg ggcatgcacg gctttgtccg tgctacgtcc cagatgttcg caacgcgtgt   2280
cagcaagtac tcgtgtgtgc tcgtagtacg tctggtggtg ggcatcgctt gtggcggccg   2340
atggcttttg gcaacggaac ggcggagcgt cgtgcaagta cgccgcaag gtgccatacg   2400 catgggcta agcttagtat gtgccgaatg ccatcagtgg ttgcgggcaa atcgggagg   2460 cgacatcgcg tcgtggcagc tgatggcttt tggcaactga acggcgaagg cctcgtgcaa   2520
gtagccccgc aaggtgccgt gcgcatgggg ctaaactcag tacgttccga ttgccatcgg   2580
ttgttgtgag ttgtgtttgg catcgctcgt ggcggttgat ggcttttggc aactgaacgg   2640
agaggcctcg tgcaagtagc gccgcaaggt gccgtgccgc attgggcta agcccagtat   2700 gttcccgatt gccatcgatt gttgcgggca acatcgggag gcgacatcgc tcgtggcggc   2760
tgataggctt ttgggcaacg gaacgcgaag gcctcgtgca agtagcgccg caagtgcccg   2820
tgcgcattgg ggctaaactc agtacgttcc gattgccatc ggttgttgtg agttgtgtct   2880
ggcattgcgt cgtggcggct gatggctttt ggcaacggaa cggcgaggcc tcgtgcaagt   2940
aggcgccgca aggtgccgtg cgcatgggc taagctcagt acgttccgat tgccatcgat   3000
tgttgcgggc aacatcggga ggcgacatcg ctcgtggcag ctgatggctt ttggcaactg   3060
aacggcgagg tctcgtgcaa gtagcgccgc aaggtgccgt gcgcatgggg catactcagt   3120
acgttccgat tgccatcgt tgttgtgagt gtgtttggc atcgctcgtg gcggttgatg   3180
gcttttggca actgaacgga gaggcctcgt gcaagtagcg ccgcaaggtg ccgttgccgc   3240 atgggctaa gccagtatgt tccgattgcc atcgattgtt gcgggccaac atcgggaggc   3300
gacatcgctc gtggcgctca tggctttggc aacggaacgg cgaggcctcg tgcaagtagc   3360
gccgcaaggt gccgtgcaca tgggctaaac tcagtacgtt ccgattgcca tcggttgttg   3420
tgagttgtgt ttggcatcgc tcgtggcggt tgatggcttt tggcaactga acggagaggc   3480
ctcgtgcaag tagcgccgca aggtgccgtg cgcatgggc aagcccagta tgttccgatt   3540
gccatcgatt gttgcgggca acatcgggag gcgacatcgc tcgtggcggc tgatggcttt   3600
```

-continued

| | |
|---|---|
| tggcaacgga acggcgaggc ctcgtgcaag tagcgccgca aggtgccgtg cgcatggggc | 3660 |
| taaactcagt acgttccgat tgccatcggt tgttgtgaag ttgtgtctgg catcgctcgt | 3720 |
| ggcggctgat ggcttttggc aacggaacgg cgaggcctcg tgcaaagtag cgccgcaagg | 3780 |
| tgccgtgcgc atgggctaag ctcagtacgt tccgattgcc atcgattgtt gcggcaaca | 3840 |
| tcggaggcg acatcgctcg tggcgactga tggcttttgg caacggaacg gcgaggcctc | 3900 |
| gtgcaagtag cgccgcaagg tgccgtgcgc atggggctaa gctaagtacg tgccggttgc | 3960 |
| catcggttgt tgtgagttgt gtctggcatc gctcgtggcg gctgatggct tttggcaacg | 4020 |
| gaacggcgag gccttgtgca gtagcgccgc aaggtgccg tgcgcatggg gctaagctca | 4080 |
| gtatgttggc attgccatcg attgttgcgg caacatcgg gaggcgacat cgctcgtggc | 4140 |
| ggctgatggc ttttggcaac ggaacggcga ggcctcgtgc aagtacgcgg cgaaggtgcc | 4200 |
| gtgcgcatgg ggctaaacta agtacgtgcc gattgccatc agttgttgtg agttgtgtct | 4260 |
| ggcatcgctc ttggcggttg atggcttttg gcaacggaac ggcgaggcct catgcacgta | 4320 |
| gcaccgcaag gtgccgtgcg catgggcta agctaagtac gtgacgattg ccatcgattg | 4380 |
| ttgggtgcaa catcgggtgg cggcatcgct cgtggcagct gatggctttt ggcaatggaa | 4440 |
| tggcgaggcc tcgtgcaagt agcgccgcaa ggtgccgtgc cgcctcgcgc ggctgagttt | 4500 |
| agtactgttg aaggtcgtgc ggttgttgtg ggttgtgtct gtggcttta tttatggcgc | 4560 |
| cttgttcgtt tatatactcc aatggttcgt gcctggcggg gcttgtcttt ggctttgcaa | 4620 |
| cgttggcatt ggcaacaaca catggcatcg cgtcgcgtgt tggggctgtt gtcggcatgt | 4680 |
| atcggcgagg caagtgtacg tgcggcacat cagtggtgtt cggcttgtgt ggctaggttg | 4740 |
| gatccctgct tgtgcagcga cgtcctagcc cgcatgccat ctcagtcatg gcacaagcgc | 4800 |
| aaattaggct tgttcggagt cggttttctg tgttgcatac ctaatgccca ggcattatca | 4860 |
| agcacaatcg gttgcctttc gccctcgcg ttcgacgtgc ggggtgaacc aaaagctgca | 4920 |
| gttgtgtccc acgccatcct cgcttcgtcg tgcgatgtct aggtccatga ctagtatgct | 4980 |
| cggactctcg gattcggtaa acgcaatggg catgggtc tcattggctc ctatctgccc | 5040 |
| aaagaatgct ccttacgaat gacggtcgtg ctcgtcttgg acttggccgt ggcctttggg | 5100 |
| tcggccatgc tcatgcggtg ccgacgtcaa tgaggaatgc | 5140 |

<210> SEQ ID NO 3
<211> LENGTH: 3232
<212> TYPE: DNA
<213> ORGANISM: S. tuberosum

<400> SEQUENCE: 3

| | |
|---|---|
| cccccccacc accttccccc tcccccaacc tcaaatccaa tcatatctaa cttttcaaaa | 60 |
| gggaggttta tgcattgctt gcatccttgg aagggaaaaa ttcaccaagt gttgaaaaat | 120 |
| aagtgccgat aataacatgt tgcgtgaaat ttactagttt gccgctaagt gttgaactat | 180 |
| atgttctatg gcgatcgaaa agttgttcaa taacgatgcc ccaatgcgag ttttttcgtg | 240 |
| acgtccgttc atttctctgc ctaatgatat gttaagggc ccaataacga tgtcgctata | 300 |
| agaggttttt cggatgtcg ggtgcgattc taaagccaag taagatgcca aggggcatgt | 360 |
| gggtctacgc aggcagcagg ggcgttccac gtccggggcc aaggcagcat cggccaaggc | 420 |
| ctgcgcgcat cggacgtggc atgtgggcat cgggcaagcg acgtcggcca acgtcaggcg | 480 |
| gcatcagcca aggcctgcac gcatcggacg tggcatgtgc gcatcgggca agcgacgtcg | 540 |
| cccaacgacg ggcagcatca gccaagggtt ggacgcatcg gacgtagcct gtgcacaacg | 600 |

```
ctcagccgac gtcggcgtgg cctggccgca ttgcccttgg cttgaacaca acgtcaggc      660 gacgtcggac gtggcatgcc cgcatcggcg tggcctgccc gcatcgccct tggcttgcac      720
acaacggtca gccgacgtcg ggcgttggcc tgcccatatt gcccttggct tgcacacaac      780
ggtcagccga cgtcggacgt ggcatgcccg catcgcggtg gcctgaccgc atcgcccttg      840
gcttgcacac atcgctcagt cgacgtcaag cgtggcctgc ccacatcgcc cttggcctgt      900
gcacatcgct cagccgacgt cgggcgtggc ctgcccacat cgcccttgtc ttgcacacat      960
cgctcagtcg aagtcggccg tggcctgccg acatcgccct tgtcttgcac acattgctaa     1020
gtcgacacgc tcggcgtggc ctgcccacat cgcccttgtc ttgcacacat cgctcagtcg     1080
acgtcgggcg tggcctgccc acatcgccct tggactgcac acaacggtca gtcgacgtcg     1140
gccgtggact gtccgcttcg gccgtggcct gcccacatcg cccttgtctt gcacacatcg     1200
ctcagtcgac gtcgggcgtg gcctgcccac atcgccttg gactgcacac aacggtcagt     1260
cgacgtcggc cgtggactgt ccgcttcggc cgtggcctgc ccacatcgcc cttgtcttgc     1320
acacatcgct cagtcgacgt cgggcgtggc ctgcccacat cgcccttgac tgcacacaac     1380
ggtcagtcga cgtcggccgt ggactgtccg cttcggccgt ggcctgccca catcgccctt     1440
gtcttgcaca catcgctcag tcgacgtcgg cgtggcctgc ccgcatcgcc cttggactgc     1500
acacaacggt cagtcgacgt cggccgtgga ctgtccgctt cggccgtggc ctgcccgcat     1560
cgcccttgga ctgcacacaa cggtcagccg acgtcggacg tggcctggcc gcatcgccct     1620
tggacggcac acaacggtca cgcgacgtcg gccgtggact gcctgcatcg gccgtggcat     1680
gcgcaacatt ggtcgaggtc tagtcgacaa catgcggatg tccatgcatt cccaaaatca     1740
aaagagtagg atcatgcata acaatatatt catctatttt ccatcatcta ttctcaacgt     1800
ttccgcctca cgtggttcgt tcgtaccaat cttcattatt tttacggttt attatttttt     1860
acgtaactat tttataaatt aaaatttact aaatttatag atctaaggtt actatattta     1920
tttgtgaatt tttggtgtta attttatatt tttttgatat tttttctatt tgttattaat     1980
ttattactaa tatttcggaa atttccgaaa aaaataaaaa ttaaaaaaaa ttgttgaaaa     2040
ctattttttt atatatataa aagtcatttg tggaagctaa tgtgtgtttg taccttagaa     2100
cgtgcatatt tgggttgtac attttcatta tgattctctg gaaaaatcat gtctactcct     2160
gtcacatggg tttttttttt ttaagcatat ataagggggg tagaggtgtt ggaggcagac     2220
tgaggcgacg gcaggcggac gtcatgggcg tcctgatggg cttagtgggc tgtgctgcgt     2280
gggcttagtg ggcgtgctgc gtgggcgttt gatggcatgc atggcttgtc cgtgctacgt     2340
cgtcgggcgc ctataaaaca tgtcgaccac cggctacaaa aacatgtcga cgaccgctcg     2400
tggggcgacc gtgtgccgcc gagggcattt ttctcgaccg ggctgaacgc gtttggtgtg     2460
gaacggcagt cgttgttttc gggcgagtgg caagtttgat ggcatcgatg ctcgtcgtgc     2520
tacgtcgtcg gaggcgctgc acgcacgggg cacgcaccgg ccaagtactg ccagacgcta     2580
tagctggacc gggcgtgggc ggtgctcgtg caagaacttt agtctgcctc caacaccttt     2640
acagtgatta aattctcaac ccccttgggc ggcgccgcaa cggcggggat agcattggcc     2700
ttgcaacgaa ggcatcggcg tcggcgcacg acatctcatg tcgggcgtcg gggtgggtgt     2760
tgggcgtgca ttttcgaagc tattcacgta cggcgcatga gtggtaatcg gcttgcgtgg     2820
ttaggttgga tccctgcttc gagcagcgca cgtcctaacc cgcatgccat gtcggtcgcg     2880
gatcaagcgc atctaggctt gtcggacgtc ggtatcctgt gctgcatacc taatgcctag     2940
```

-continued

| | | |
|---|---|---|
| gcattactca cgtgcaatcg gtcgcctttc gccccctcgca ttccatgtgc ggggtgaacc | 3000 |
| caaaagccgc tcttgcgtcc cacgccttcc tcgcttcgtc gtgcgatggc gtggtcgcga | 3060 |
| gcggcggctg gaattctcgg attcggtaga cgcagtgggc atggggcctt caccggctcc | 3120 |
| tatctgccca aaacgaatgc tccttgcgaa cgacggccgc gctcgccttg acccgtccg | 3180 |
| tgcctcacgg gtgcggcggg ctcatgcggc gcgcggcgtc gctgaggaat gc | 3232 |

<210> SEQ ID NO 4
<211> LENGTH: 3253
<212> TYPE: DNA
<213> ORGANISM: L. esculentum

<400> SEQUENCE: 4

| | | |
|---|---|---|
| cccccccaca ctcccctcc cccaaaatca atccaatca tttctaactt ttcaaatgtg | 60 |
| aggttcgcgt gctgcctgca tccttcgaag aggaaaaaat aactaagtgt tgaaatataa | 120 |
| gtttcaaaag taacacggca agtgaagttc actagtctgc cgctaagtgt tgagctatgc | 180 |
| gttctgagcc ccattgcgag ttttcgtga agttgagttc atttatcaag cctaatgaca | 240 |
| tgttaaggga ctaatgacat gtcactgtaa gaggttttcg ggatgtcggg tgcgattatt | 300 |
| aaagccaagt tagatgtcaa ggggcaaatg ggtctgcgta cgcagcacgt ccgcggccag | 360 |
| gcggcatctg caaaggcctg cgccgaacgg cgtggactgc aaaatacgcc tttgggcagc | 420 |
| acacacggtc gaacgacgtc gggcgtggca tgtcatcatc gcctttgggc agcacacacg | 480 |
| ttcgagcgac gtcgggcgtg gcatgccatc atcgcctttg gcagtacac acggtcgaac | 540 |
| gacgtcgggc gtggcatgcc accatcgcct ttgggcagca cacacggtcg agcgacgtcg | 600 |
| ggcgtggcat gccatcatcg cctttgggca cacacggtcg aacggcgtct ggcgtggcat | 660 |
| gccatcttcg cctttttgca gcacacacgg tcgaacgacg tcgggcgtgg catgccatct | 720 |
| tcgcccttg acagcataga cggtcggccg tcgtcgggcg tggcatgcca tcttcgcct | 780 |
| ttgacagcat agacggtcgg ccgtcgtcgg gcgtggcatg ccatcatagc ccttggacag | 840 |
| cacaaacggt cggccgtcgt cggacgtgcc tgcacacaac ggtcggccgt ggcctgcccg | 900 |
| catcggtcgt ggcttgcgca acattcatcg agttccaaac aaaacatgcg gatgttcatg | 960 |
| gcgtacataa atcaaaggat tttgaaacaa cctccatgca taacaaacat attcatctac | 1020 |
| tttccattat ctattctcaa acgtttccgc ctaacgtggc tctttcgcat cattttcgtt | 1080 |
| acttttacgg ttcgtacgat attgaaacat cttttgtttg tgcaaatatg catcttatca | 1140 |
| ttaatttgac atgttgagaa gtgttttcga gcatttccat attttttccga cttttaatca | 1200 |
| ttattttata atttattttt acgctttttt aatttttacg tctcttttta aaaattaaaa | 1260 |
| tttattaaat tttatatttt aaggttcaca tatttatttg tgaattttcg gagttgattt | 1320 |
| catatttttt cgatatttc cctattttt attaatttat tactaatttt ttggaattt | 1380 |
| tgaaaaaaat aaaaatcaaa aaaattgtt gaaaaatatt tttttataca tattaaagtc | 1440 |
| aattatgaag gctgatgtgt gtttgtacct tagaccgcgc atatttgggt tgtacatttt | 1500 |
| cattatgatt ctctggaaaa tccatgtcta ctcctgtcac atgggcaaaa ctttttttaag | 1560 |
| catatataag ggggtagag gtgttggagg cagactgagg cgcaggcagg cagacggcat | 1620 |
| aggcgtcccg tgggcttagc aggcgtgctg cgtgggcgct tgatggcatg catggcttgt | 1680 |
| ccgtgctacg ccgttgggcg tttacaaaaa cacgtcggcg acgtcgacgg gtcgagtggg | 1740 |
| caacggcagg cggacgccga gggcatcctg tgggcttagt aggcgtgctg cgtgggcgct | 1800 |
| tgatggcatg catggctcgt ccgtgctacg tcgttgggcg tctacaaaaa catgctagcg | 1860 |

```
acgtttgcgg ggcaactgaa gcgaaggcag gcggacgtcg agggcgtcct gtgggcttag    1920
taggcgtgct gcgtgggcgc ttgacggcat gcatggctcg tccgtgctac gccgttgggc    1980
gtttacaaaa acacgcccgc gacgtctgta gggcgtttga ggcggtggca ggcggacgtc    2040
atgggcgtcc tgtgggctta gtaggtgtgc tgcgtgggcg cttgacggca tgcatggctc    2100
gtccgtgcta cgccgttggg cgtcaacaaa aacatgccag cgacgtctgc ggggcaactg    2160
aggcgaaagc aggcggacgt caagggcgtc ctgtgggctt agtaggcgtg ctgcgtgggc    2220
gcttgatggc atgcatggct cgtccgtcgt acgccgttgg gcgcttgcaa aaacatgtcg    2280
acgacgtctg cggggcgacc gaggcgttac aaggcggatg ccatgggcgt cctgtgggct    2340
tagtaggcgt gctgcgtggg agcttgatgg catgcatggc tcgtccgtgc tacgccgttg    2400
ggcgcttaca aaaacatgcc agcgacgtct gcggggcgaa cgtgcgccgc cgagggaact    2460
tctcaagatc ggttttatta ttgcgtttgg tgtggaaacg gcagtgcttt cgggcgagtg    2520
gcgagttcta gagctcctgt tacggctaac tctaggcgtc gcacgcacgg ggcacgtaag    2580
gccatgtacg gccagacgct atgatggacc gggcgtgggc ggttccctg tgtgaacctt    2640 ggtcttcctc caacaatctt tgcagtgatt aaattctcaa ctcccttggg cggcgcgcaa    2700
cggcgggtgt agcattggcc ttgcaaagaa ggcatcggcg tcgtcgcacg acatctaatg    2760
tcgggcggcg gggtggatgt cgggcgtgca tttccggagc tattcacgta cggcgcatga    2820
gtggtattgg gcatgtgtgg ttaggttgga tccctgcttc gagcagcgac gtcctaactc    2880
gcatgccaac tcggtgacgg atgaagcgca atctaggctg gtcggacgtc ggaacttcct    2940
gtgctgcata cctactgcct aggcattgtg cacgtgcaaa cggtcgcctt tcgcccctcg    3000
catcccatgc gcggggtgaa cccaaaagac gctctcgcgt cccacgcctt ccctcgcttc    3060
gtcgtgcgat ggcgtggtcc gtgagcggcg cctcgaattc tcggatacgg tagacgcagt    3120
gggcatgggg ccttcaccgg cttctatctg cccaaaacga atgctccttg cgaatgactg    3180
ccgcgctcgc cttggacccg accgtgcccg aaaggcgccg ggctcatgcg ggcgcggcgt    3240
cgttgaggaa tgc                                                       3253
```